United States Patent [19]

Speranza et al.

[11] Patent Number: 5,064,571
[45] Date of Patent: Nov. 12, 1991

[54] MIXTURES OF FATTY AMIDO-AMINES FROM POLYOXYALKYLENEAMINES

[75] Inventors: George P. Speranza; Carter G. Naylor, both of Austin; Jiang-Jen Lin, Houston, all of Tex.

[73] Assignee: Texaco Chemical Company, White Plains, N.Y.

[21] Appl. No.: 392,313

[22] Filed: Aug. 11, 1989

[51] Int. Cl.$^5$ .................. B01F 17/16; B01F 17/22; C11D 1/40; C11D 1/52
[52] U.S. Cl. .................... 252/357; 252/61; 252/307; 252/356; 252/392; 252/542; 252/546; 252/548; 252/DIG. 1
[58] Field of Search ............... 252/307, 356, 357, 542, 252/546, 548, DIG. 1, 392; 564/192

[56] References Cited

U.S. PATENT DOCUMENTS

| | | | |
|---|---|---|---|
| 2,429,445 | 10/1947 | Young et al. | 252/548 |
| 2,540,678 | 2/1951 | Kelley | 252/357 X |
| 2,675,355 | 4/1954 | Lytle | 252/392 X |
| 2,679,504 | 5/1954 | Katzman | 252/357 X |
| 2,710,856 | 6/1955 | Carpenter | 252/357 X |
| 2,739,980 | 3/1956 | Chester | 252/548 X |
| 2,992,994 | 7/1961 | Albrecht et al. | 252/548 |
| 3,166,548 | 1/1965 | Kirkpatrick et al. | 252/357 X |
| 3,262,951 | 7/1966 | Katz | 252/357 X |
| 4,405,494 | 9/1983 | Oppenlaender et al. | 252/357 X |
| 4,560,497 | 12/1985 | Staker et al. | 252/392 |
| 4,828,757 | 5/1989 | Naylor et al. | 252/DIG. 1 |

Primary Examiner—Richard D. Lovering
Attorney, Agent, or Firm—Jack H. Park; Kenneth R. Priem; David L. Mossman

[57] ABSTRACT

Novel fatty amines, amides and salts thereof may be made from the reaction of polyoxyalkylenepolyamine residues with fatty acids and/or fatty acid esters under relatively mild reaction conditions in the absence of a catalyst. Remarkably, the residues or bottoms products from the synthesis of polyoxyalkylenepolyamines, such as triethylene glycol diamine and tetraethylene glycol diamine, also known as JEFFAMINE ® EDR amines, may be reacted with the fatty acids and/or fatty acid esters to give materials useful in corrosion inhibitors, pigment wetting agents, mineral flotation and flocculation aids, asphalt emulsifiers, surfactants, detergents, petroleum additives, etc.

21 Claims, No Drawings

MIXTURES OF FATTY AMIDO-AMINES FROM POLYOXYALKYLENEAMINES

FIELD OF THE INVENTION

The invention relates to bottoms products or residues from the manufacture of polyoxyalkyleneamines, and, in one aspect, more particularly relates to fatty amines prepared by the reaction of such bottoms products with fatty acids.

BACKGROUND OF THE INVENTION

Triethylene and tetraethylene glycol diamines may be continuously produced from glycols catalytically. The triethylene glycol diamine and tetraethylene glycol diamine products are known under the trade names JEFFAMINE® EDR-148 and JEFFAMINE® EDR-192, respectively, as made by Texaco Chemical Co. These materials are useful as intermediates in the preparation of hydrophilic nylon resins, and as epoxy curing agents. However, in the production of polyethylene glycol diamine, due to the moderate conversions, there are also produced significant quantities of bottoms products or residues, and it would be beneficial if uses for these materials could be discovered.

It is known to react fatty acids with amines, generally, although not the polyethylene glycol polyamines described above. For instance, the reaction of a fatty acid of the formula RCOOH, where R is a long chain alkyl group with the amine on the left produces the compound on the right:

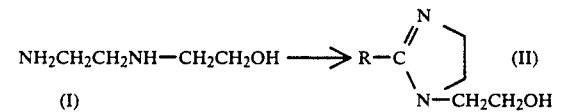

(I)      (II)

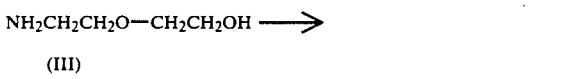

(III)

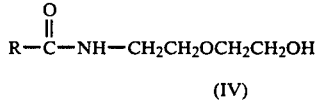

(IV)

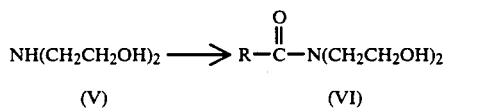

(V)      (VI)

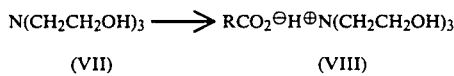

(VII)      (VIII)

A general reference for surfactant chemistry of this type is M. J. Rosen, *Surfactants and Interfacial Phenomenon*, John Wiley and Sons, 1978.

In another brief example, the reaction of oleic acid with diethylene triamine may give fatty amine compounds, also known as imidazolines, which have the following structure:

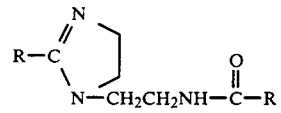

In the making of conventional fatty amido-amines, an alkylene oxide may be added to the amine. Fatty amines, which include related amides and salts, are important in industrial applications such as corrosion inhibitors, pigment wetting agents, mineral flotation and flocculation aids, asphalt emulsifiers, surfactants, petroleum additives, etc. The fatty amines are also used as raw materials in the production of amine oxides, quaternary ammonium salts, cationic emulsifiers, and ethoxylates and propoxylate derivatives.

SUMMARY OF THE INVENTION

Accordingly, it is an object of the present invention to provide mixtures of novel fatty amines, which herein are defined as including amido-amines and salts thereof, that may be made from bottoms products or residues from other processes.

It is another object of the present invention to provide mixtures of fatty amines that may be simply produced.

Another object of the invention is to provide novel mixtures of fatty amines that may have a wide range of uses.

In carrying out these and other objects of the invention, there is provided, in one form, mixtures of fatty amines prepared by a process involving reacting at least one first component including at least one compound selected from the group of fatty acids and fatty acid esters, with a second component including at least one polyoxyalkyleneamine residue.

DETAILED DESCRIPTION OF THE INVENTION

It has been discovered that novel fatty amines may be prepared by the reaction of fatty acids, such as oleic acid for example, with polyoxyalkyleneamine residues. The amines used to make the novel fatty amines may be bottoms products or residues, such as from the JEFFAMINE® EDR amines process, and may contain mixtures of triethylene glycol monoamines, triethylene glycol diamine, tetraethylene glycol mono and diamines and condensation products from the process. In this way, otherwise undesirable bottoms products may be usefully employed.

It will be appreciated that the reaction product of this invention will be a complex mixture of amines and/or amides, sometimes called amido-amines. Other possible product structures will be discussed below. The fact that a complex mixture is produced does not reduce their ability to perform as useful components in the various formulations discussed, e.g., surfactants, detergents, etc.

One component or co-reactant, sometimes called the first component herein, is selected from fatty acids, fatty acid esters or mixtures thereof. Suitable fatty acids may be defined as RCOOH, where R is a linear or branched alkyl, alicyclic or alkylene group of from about 9 to 23 carbon atoms, and in a narrower aspect from about 11 to 17 carbon atoms. The suitable fatty acid esters have structures of RCOOR' where R and R' are alkyl groups having a R+R' sum of carbon atoms within the ranges set out above. The fatty acids and esters may be cyclic as well.

The use of dicarboxylic acids may give materials such as the following and mixtures thereof. The first two structures shown are simply two possible structures depending on how the ring reacts.

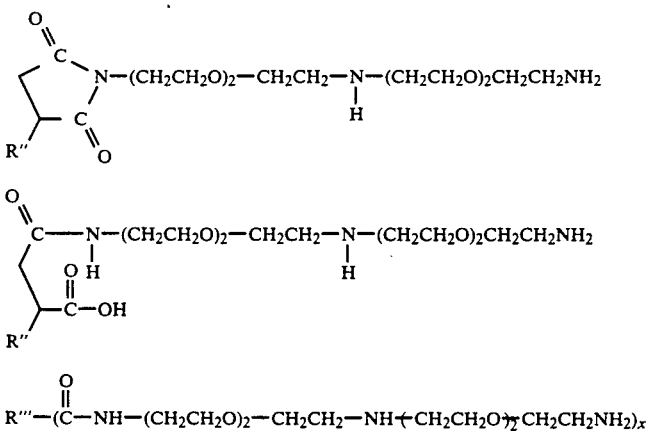

where R" and R'" have from 60-100 carbon atoms, and x ranges from 1 to 3. The fatty acids and fatty acid esters need not be only monoacids or monoesters. Di- and polyacids and esters may also be employed, such as those prepared from linoleic or other unsaturated fatty acids. For example, dimer acids may be represented as R"—(COOH)$_2$, where R" may range from about 8 to 34.

The second or amine component will now be described. The principal products of the JEFFAMINE ® EDR amine process are triethylene glycol diamine and tetraethylene glycol diamine, known under the trade names JEFFAMINE ® EDR-148 and JEFFAMINE ® EDR-192, respectively. The numbers refer to the approximate molecular weight. These compounds have the following respective structures:

NH$_2$—CH$_2$CH$_2$OCH$_2$CH$_2$OCH$_2$CH$_2$—NH$_2$ and

NH$_2$—CH$_2$CH$_2$OCH$_2$CH$_2$OCH$_2$CH$_2$OCH$_2$CH$_2$—NH$_2$.

While the residues from these processes have not been completely identified, they are known to contain mixtures of triethylene glycol mono- and diamines, and condensation products such as:

NH$_2$(CH$_2$CH$_2$O)$_2$—CH$_2$CH$_2$—NH—(CH$_2$CH$_2$O)$_2$—CH$_2$CH$_2$NH$_2$,

NH$_2$—(CH$_2$CH$_2$O)$_2$—CH$_2$CH$_2$NH—(CH$_2$CH$_2$O)$_2$—,—CH$_2$CH$_2$OH etc. Bottoms products from any process will vary somewhat, and are thus difficult to define with precision. The bottoms products from the JEFFAMINE ® EDR process will vary depending on the temperature and pressure which they are subjected to. It will be appreciated that although one aspect of this invention contemplates the use of JEFFAMINE ® EDR residues, that the invention need not be limited to such particular residues, but may apply to any amine residues or bottoms products or mixture thereof, or even mixture of residues with relatively more pure amines, regardless of whether or not they are exemplified by structure or name herein, that fall within the claimed definitions. The use of relatively more pure amines with the amine residues or bottoms products may help improve the resulting novel fatty amines in some way. In one aspect of the invention, at least 50% of the second, amine component should be polyoxyalkyleneamine residue.

The reaction to make the novel fatty amines herein may be performed simply and easily. The reaction temperature ranges from ambient for the preparation of salts to 280° C. for the preparation of amides. Pressures may range from atmospheric to 200 psig, although reduced pressures may also be used.

The materials of this invention will be useful as corrosion inhibitors, pigment wetting agents, mineral flotation and flocculation aids, asphalt emulsifiers, antistrip agents, biocides, viscosity modifiers, petroleum additives, and as surfactants. The ease of preparation of the salts and the polyamines without knowing the precise composition of the amines is achieved. As will be shown, the interfacial tension values for the polyether amine fatty acid salts were remarkably low, indicating suitability for use in surfactants and detergents; see Tables II and IV. The invention will be illustrated further by the following examples which are not intended to limit the scope of the invention. It will be remembered that the amines of this invention are defined to include amides and salts thereof.

EXAMPLE 1

Reaction of Oleic Acid with Residues from JEFFAMINE ® EDR-148 Amine Process

The residues were wiped-film evaporator bottoms (see Table I for analysis). To a 500-ml 3-necked flask equipped with a stirrer and thermometer were added 282.5 g. of oleic acid and 149 g. of EDR-148 residues. The mixture was stirred for one hour at 40° to 60° C. Then 215 g. of this salt was removed (denoted as 6152-64S). The remainder was heated for about four hours at 220° C., during which time 8 ml of water was collected. The product was then heated at 200° C. and one mm for one hour; this product was denoted as 6152-64A.

TABLE I

| | Bottoms Products Characterizations | |
|---|---|---|
| | EDR-148 Bottoms | EDR-192 Bottoms |
| Total acetylatables | 6.72 meq/g | 7.08 |
| Total amine | 4.37 | 6.06 |
| Primary amine | 2.56 | 2.92 |
| Sec. & Tert. amine | 1.81 | 3.14 |

TABLE I-continued

| | Bottoms Products Characterizations | |
|---|---|---|
| | EDR-148 Bottoms | EDR-192 Bottoms |
| Source | Wiped film evaporator bottoms | Still bottoms |

EXAMPLE 2

Reaction of Oleic Acid with Residues from JEFFAMINE ® EDR-192 Amine Process

To a 500 ml 3-necked flask equipped with a stirrer, thermometer and Dean Stark trap were added 141.3 g. of oleic acid and 83 g. of EDR-192 residue. The contents were stirred for 50 minutes and then sampled and designated as 6152-97S. The remainder was heated from 168° C. to 214° C. over a four-hour period. During this period 7 ml of water was collected overhead. The material was heated further at 1 mm and 200° C. The product, denoted as 6152-97A, was a dark brown liquid.

EXAMPLE 3

Tension Values of Amides and Salts

The surface activity of these oleic acid derivatives of JEFFAMINE ® EDR-148 and EDR-192 residues were examined. The data are summarized in Table II. Our observations show that the salts are highly soluble soaps of oleic acid neutralized by the polyether amines (6152-64S and -97S). At alkaline pH they displayed excellent surface tension and interfacial tension values. Their solubility declines at acidic pH and in the cases presented the interfacial tension values decline and the solutions become nonhomogeneous with decreasing pH. The oleamides (6152-67A and -97A) gave very low measured surface tensions, although the solubility at pH 6 and 8 was low. The material -64A was also poorly soluble at pH 4, but sample -97A was almost completely soluble at pH 4; its surface and interfacial tension values are characteristic of cationic surfactants.

The oleamide of EDR-192 bottoms, sample -97A, apparently contains enough free amine groups to be protonated at pH 4. That of EDR-148 bottoms, sample -64A, does not. This is evidence that these residues contain little or no tertiary amine. The non-primary amine is assumed to be secondary. The residues from EDR amines processing can thus clearly be utilized in surfactant applications. The reactive amounts of soap and amide may be varied by varying the residue:fatty acid equivalent ratio and the severity of condensation conditions. Thus, these products will be useful as corrosion inhibitors, asphalt emulsifiers, thickeners and the like.

The comparative examples of Table II show that the oleate salt compositions of Examples I and II have comparable surface tensions and superior interfacial tensions.

TABLE II

Tension Values of JEFFAMINE ® EDR Amine Bottoms

| Ex. | Derivative | pH | Appearance, 0.10% | Tension @ 25° C., 0.10% Surface | Tension @ 25° C., 0.10% Interfacial |
|---|---|---|---|---|---|
| 1 | EDR-148 Bottoms | 8.0 | Mostly oiled out | 29.2 | 0.4 |
| | Oleamide | 6.0 | Nearly all oiled out | — | — |
| | (6152-64A) | 4.0 | Mostly oiled out | 31.0 | 0.7 |
| | EDR-148 Bottoms | 10.0 | Clear | 30.8 | 2.9 |
| | Oleate Salt | 8.0 | Hazy | 28.0 | 1.0 |
| | (6152-64S) | 6.0 | Some solid ppt. | 27.8 | 8.8 |
| 2 | EDR-192 Bottoms | 8.0 | Mostly oiled out | 27.9 | 0.7 |
| | Oleamide | 6.0 | Less oiled out | 34.4 | 0.8 |
| | (6152-97A) | 4.0 | Slightly hazy | 42.9 | 10.8 |
| | EDR-192 Bottoms | 10.0 | Clear | 28.7 | 3.0 |
| | Oleate Salt | 8.0 | Slightly hazy | 28.4 | 0.4 |
| | (6152-97S) | 6.0 | Some solid ppt. | 28.3 | 14.8 |
| Comp. 1 | EDR-148 Bottoms Oleate Salt | 9.0 | Clear | 27.5 | 4.0 |
| Comp. 2 | EDR-192 Bottoms Oleate Salt | 9.0 | Clear | 27.9 | 2.3 |
| Comp. 3 | Monoethanolamine Oleate Salt | 9.0 | Clear | 27.4 | 6.6 |
| Comp. 4 | Sodium Oleate Salt | 9.0 | Clear | 28.4 | 8.6 |

EXAMPLES 4

Reaction of Fatty Acids with Residues from JEFFAMINE ® EDR-148 Amine Process

Fatty acids were condensed with the bottoms obtained from a commercial JEFFAMINE ® EDR-148 production run according to the procedures outlined in Example 1. The EDR bottoms had the following analysis:

| | |
|---|---|
| Density @ 20° C., g/cm$^3$ | 1.0784 |
| Total acetylatables, meq/g | 9.51 |
| Total amine, meq/g | 7.90 |
| Primary amine, meq/g | 4.07 |
| Tertiary amine, meq/g | 0.09 |

It consisted of about:

| | |
|---|---|
| $[H_2NCH_2CH_2OCH_2CH_2OCH_2CH_2]_2NH$ | 60% |
| $H_2NCH_2CH_2OCH_2CH_2OCH_2CH_2NH[CH_2CH_2O]_3H$ | 40% |

The fatty acid:EDR bottoms primary amine content equivalent ratio for the condensations was 1:1. Analyses of the amide derivatives are summarized in Table III. All the samples were basic, indicating that they contained free amine groups.

TABLE III

Amide Derivatives of JEFFAMINE ® EDR-148 Bottoms

| | | Amide analysis, meq/g | | | |
|---|---|---|---|---|---|
| Sample | Acid | Total amine | Primary amine | Sec. amine | Tert. amine |
| A | Lauric | 2.25 | 0.03 | 2.18 | 0.04 |
| B | Myristic | 2.11 | 0.09 | 1.98 | 0.03 |

TABLE III-continued

Amide Derivatives of JEFFAMINE ® EDR-148 Bottoms

| Sample | Acid | Amide analysis, meq/g | | | |
|---|---|---|---|---|---|
| | | Total amine | Primary amine | Sec. amine | Tert. amine |
| C | Palmitic | 1.95 | 0.21 | 1.70 | 0.04 |
| D | Dimer | 2.05 | 1.75 | 0.27 | 0.03 |
| E | Dodecenyl succinic | 2.00 | 0.44 | 1.52 | 0.04 |
| F | Dodecenyl succinic | 1.88 | 0.08 | 1.77 | 0.04 |

TABLE IV

AMIDE DERIVATIVES OF JEFFAMINE ® EDR-148 BOTTOMS

| Sample | Amide | Appearance 10% solution of HCl salt | Tension at pH 6, 0.10% | | Foam height, 49° C., 0.10% | |
|---|---|---|---|---|---|---|
| | | | Surface | Interfacial | Initial | After 5 min. |
| A | Lauramide | Amber solution, hazy | 33.9 dynes/cm | 4.8 dynes/cm | 131 mm | 131 mm |
| B | Myristamide | Same | 37.7 | 4.8 | 89 | 89 |
| C | Palmitamide | Same | 41.9 | 12.3 | 41 | 6 |
| D | Dimer acid diamide | Same | 52.6 | 21.2 | 50 | 3 |
| E | Dodecenylsuccinamide | Clear yellow solution | 32.1 (pH 9) | 2.8 (pH 9) | 81 | 7 |
| F | Dodecenylsuccinamide | Clear, light-amber solution | 30.8 | 2.4 | 132 | 99 |

EXAMPLE 5

Tension Values and Foaming Power of Amides

The samples of Table III were dissolved in water with the aid of hydrochloric acid. Sample E was soluble without added acid. Tension values and foaming power were measured for the samples at 0.10% concentration. The data, summarized in Table IV, provide more evidence for the very good surface active properties of the subject compositions, indicating the suitability for use in surfactants and detergents.

Many modifications may be made in the method and products of the present invention without departing from the spirit and scope of the invention which are defined only by the appended claims. For example, one skilled in the art may use a particular composition of polyoxy-alkylene polyamines, or a particular mixture of fatty acids and/or fatty acid esters, or kind and proportions of reactants, or particular reaction conditions to produce novel fatty amines with certain advantageous properties.

We claim:

1. Mixtures of amido-amines prepared by a process comprising reacting at least one first component comprising at least one compound selected from the group consisting of mono- and dicarboxylic acids and acid esters, with a second component comprising polyoxyalkyleneamine bottoms products, where the reaction is conducted in the temperature range from about 25° to about 280° C. and at a pressure in the range from about atmospheric to about 200 psig.

2. The mixtures of amido-amines and of claim 1 wherein the polyoxyalkyleneamine bottoms products are selected from the group consisting of bottoms products from the reductive amination of triethylene glycol, the reductive amination of tetraethylene glycol, the hydrogenation of acrylonitrile adducts of polyethylene glycols, the hydrogenation of acrylonitrile adducts of polypropylene glycols, and mixtures thereof.

3. The mixtures of amido-amines of claim 1 where the polyoxyalkyleneamine bottoms products are selected from the group consisting of alkylene glycol polyamine bottoms products.

4. The mixtures of amido-amines of claim 1 where the polyoxyalkyleneamine bottoms products are selected from the group consisting of ethylene glycol polyamine bottoms products.

5. The mixtures of amido-amines of claim 4 where the polyoxyalkyleneamine bottoms products are selected from the group consisting of triethylene glycol diamine bottoms products, tetraethylene glycol diamine bottoms products, and mixtures thereof.

6. The mixtures of amido-amines of claim 4 where the second component comprises greater than 50% of the polyoxyalkyleneamine bottoms products.

7. The mixtures of amido-amines of claim 1 wherein the mono- and dicarboxylic acids and acid esters are fatty acids and fatty acids esters and the mixtures of amido-amines and esteramines produced of fatty amido-amines and esteramines.

8. Inorganic salts of the mixtures of amido-amines of claim 1.

9. Mixtures of fatty amido-amines prepared by a process comprising reacting at least one first component comprising at least one compound selected from the group consisting of fatty acids and fatty acid esters having from about 9 to 34 carbon atoms, with a second component comprising polyoxyalkyleneamine bottoms products selected from the group consisting of bottoms products from the reductive amination of triethylene glycol, the reductive amination of tetraethylene glycol, the hydrogenation of acrylonitrile adducts of polyethylene glycols, the hydrogenation of acrylonitrile adducts of polypropylene glycols, and mixtures thereof, where the reaction is conducted in the temperature range from about 25° to about 280° C. and at a pressure in the range from about atmospheric to about 200 psig.

10. The mixtures of fatty amido-amines of claim 9 where the second component comprises greater than 50% of the polyoxyalkylene amine bottoms products.

11. Inorganic salts of the mixtures of fatty amido-amines of claim 9.

12. Mixtures of fatty amido-amines prepared by a process comprising reacting at least one first component comprising at least one compound selected from the group consisting of fatty acids and fatty acid esters having from about 9 to 34 carbon atoms, with a second component comprising polyoxyalkyleneamine bottoms products selected from the group consisting of polyoxyalkylene bottoms products, where the reaction is conducted in the temperature range from about 25° to about 280° C. and at a pressure in the range from about atmospheric to about 200 psig.

13. The mixtures of fatty amido-amines of claim 12 where the second component comprises greater than 50% of the polyoxyalkyleneamine bottoms products.

14. Inorganic salts of the mixtures of fatty amidoamines of claim 12.

15. A method for making mixtures of fatty amidoamines comprising reacting at least one first component comprising at least one compound selected from the group consisting of fatty acids and fatty acid esters, with a second component comprising polyoxyalkyleneamine bottoms products, where the reaction is conducted in the temperature range from about 25° to about 280° C. and at a pressure in the range from about atmospheric to about 200 psig.

16. The method of claim 15 where the polyoxyalkyleneamine bottoms products are selected from the group consisting of bottoms products from the reductive amination of triethylene glycol, the reductive amination of tetraethylene glycol, the hydrogenation of acrylonitrile adducts of polyethylene glycols, the hydrogenation of acrylonitrile adducts of polypropylene glycols, and mixtures thereof.

17. The method of claim 15 where the polyoxyalkyleneamine bottoms products are selected from the groups consisting of alkylene glycol polyamine bottoms products.

18. The method of claim 17, where the polyoxyalkyleneamine bottoms products are selected from the group consisting of ethylene glycol polyamine bottoms products.

19. The method of claim 18 where the polyoxyalkyleneamine bottoms products are selected from the group consisting of triethylene glycol diamine bottoms products, tetraethylene glycol diamine bottoms products, and mixtures thereof.

20. The method of claim 15 where the second component comprises greater than 50% of the polyoxyalkyleneamine bottoms products.

21. The method of claim 15 where the first component is a fatty acid, fatty acid ester or mixture thereof having 9 to 34 carbon atoms.

* * * * *

UNITED STATES PATENT AND TRADEMARK OFFICE
CERTIFICATE OF CORRECTION

PATENT NO. : 5,064,571

DATED : November 12, 1991

INVENTOR(S) : George P. Speranza; Carter G. Naylor; Jiang-Jen Lin

It is certified that error appears in the above-identified patent and that said Letters Patent is hereby corrected as shown below:

Column 7, line 59, claim 2, the word "and" should be deleted.

Column 8, line 30, claim 7, the word "acids" at its second occurrence preceding "esters" should be deleted and replaced by the word --acid--. In line 31, after the word "produced" and before the word "of", the words --are mixtures-- should be added.

Signed and Sealed this

Twenty-second Day of June, 1993

Attest:

MICHAEL K. KIRK

Attesting Officer

Acting Commissioner of Patents and Trademarks